US006210552B1

(12) United States Patent
Mizutani et al.

(10) Patent No.: US 6,210,552 B1
(45) Date of Patent: Apr. 3, 2001

(54) OXYGEN SENSOR

(75) Inventors: Akio Mizutani, Nagoya; Teppei Okawa, Kounan; Hiroshi Isomura, Komaki; Hiroshi Kubota, Wako; Seiichi Hosogai, Wako; Hiroyuki Fujita, Wako, all of (JP)

(73) Assignees: NGK Spark Plug Co., Ltd., Aichi; Honda Motor Co., Ltd., Tokyo, both of (JP)

( * ) Notice: Subject to any disclaimer, the term of this patent is extended or adjusted under 35 U.S.C. 154(b) by 0 days.

(21) Appl. No.: 09/199,319

(22) Filed: Nov. 25, 1998

(30) Foreign Application Priority Data

Nov. 25, 1997 (JP) .................................... 9-323288

(51) Int. Cl.$^7$ ................................................ G01N 27/407
(52) U.S. Cl. ........................ 204/429; 204/428; 427/125
(58) Field of Search ...................... 204/421–429

(56) References Cited

U.S. PATENT DOCUMENTS

| 4,107,019 | * | 8/1978 | Takao et al. | 204/426 |
| 4,151,503 | * | 4/1979 | Cermak et al. | 204/424 |
| 4,225,634 | * | 9/1980 | Tanaka et al. | 204/429 |
| 4,851,105 | | 7/1989 | Ishiguro et al. . | |
| 5,160,598 | * | 11/1992 | Sawada et al. | 204/429 |
| 5,271,821 | * | 12/1993 | Ogasawara et al. | 204/429 |
| 5,443,711 | | 8/1995 | Kojima et al. . | |

FOREIGN PATENT DOCUMENTS

| 50-14396 | 2/1975 | (JP) . |
| 53-50888 | 5/1978 | (JP) . |
| 54-89686 | 7/1979 | (JP) . |
| 55-020423 | 2/1980 | (JP) . |
| 58-099747 | 6/1983 | (JP) . |
| 01232253 | 9/1989 | (JP) . |

* cited by examiner

*Primary Examiner*—T. Tung
(74) *Attorney, Agent, or Firm*—Sughrue, Mion, Zinn, Macpeak & Seas, PLLC

(57) ABSTRACT

There is disclosed an oxygen sensor disposed before an exhaust gas purifying catalyst of an engine which uses a hydrocarbon containing fuel with a H/C ratio of three or more. An oxygen sensor 1 is provided with a solid electrolytic body 2 which can generate a difference in oxygen concentration with reference gas and measured gas, a reference electrode 3 and a detection electrode 4 formed on inner and outer surfaces of the solid electrolytic body 2, and a porous protective layer 5 for covering the detection electrode 4. The detection electrode 4 is formed only of a metal like Pt which promotes oxidizing reaction of methane to have a thickness of 1 to 2 $\mu$m. In the protective layer 5, only a second protective layer 5b carries Pt catalyst 6 which promotes oxidizing reaction of hydrogen, and the amount of carried catalyst is in the range of 0.5 to 7 mol % relative to the whole of the second protective layer 5b. According to the oxygen sensor 1, even if a large amount of hydrogen is exhausted, for example, from CNG engine, or even if a large amount of methane is exhausted, an excellent engine control can be realized.

20 Claims, 4 Drawing Sheets

RELATIONSHIP OF FILM THICKNESS
AND
CONTROL POINT

OXYGEN SENSOR

BACKGROUND OF THE INVENTION (i) Field of the Invention

The present invention relates to an oxygen sensor disposed before an exhaust gas purifying catalyst of an engine which uses a hydrocarbon containing fuel with a ratio of hydrogen atoms and carbon atoms, i.e., H/C ratio of three or more.

(ii) Description of the Related Art

Various researches and proposals have been developed as conventional oxygen sensors for gasoline engines. For example, Examined Japanese Patent Publication No. Hei 8-7177 discloses an oxygen sensor which is superior in durability, can effectively use a noble-metal catalyst and which can keep stable an air/fuel ratio control for a long time without deviation from the stoichiometric point or deterioration in responsiveness.

Specifically, the oxygen sensor is provided with a reference electrode disposed on a surface of a solid electrolytic body having an oxygen ion conductivity, a detection electrode disposed on the other surface of the solid electrolytic body, a first porous protective layer disposed to cover the detection electrode, and a second porous protective layer disposed on the first protective layer. For example, the detection electrode is formed into a thickness of 0.9 $\mu$m by chemical plating of platinum, the first protective layer is formed by plasma spray coating of spinel powder, and the second protective layer is formed by baking titania paste containing a noble metal catalyst. Additionally, the second protective layer contains 0.02 to 5 mol % of noble metal catalyst.

However, a preferable oxygen sensor has not been proposed which is disposed before or upstream from an exhaust gas purifying catalyst of an engine which uses CNG (compressed natural gas) fuel or another hydrocarbon containing fuel with a ratio of hydrogen atoms and carbon atoms, i.e., H/C ratio of three or more.

Moreover, for example, a CNG engine car contains a larger amount of hydrogen and methane in its exhaust gas than a gasoline engine car. Therefore, if the oxygen sensor for the gasoline engine is mounted upstream from the catalyst for purifying the exhaust gas of the CNG engine, and is continuously used for engine control, the undermentioned problems (1) and (2) arise:

In this case, the oxygen sensor for the gasoline engine is provided with a 0.9 to 1 mm thick solid electrolyte of zirconia; a reference electrode and a detection electrode, each of a 0.9 $\mu$m thick platinum layer, formed inside and outside the solid electrolyte; a 100 $\mu$m thick first protective layer of spinel for covering the reference electrode; and a 50 $\mu$m thick second protective layer of titania powder for covering the first protective layer. The catalyst of platinum is contained by 0.4 mol % in the entire second protective layer (1) When the oxygen sensor is continuously used in the flow of exhaust gas, the catalyst in the second protective layer is sublimated and scattered, the capability of oxidizing hydrogen is deteriorated, engine control is deviated toward the lean side, and nitrogen oxides are increased.

(2) When the oxygen sensor is continuously used in the flow of exhaust gas, especially on operation condition that a large amount of methane is exhausted, e.g., on operation condition that a small load is applied and the number of revolutions is large, the circumstance is that engine control is deviated toward the lean side as in the above (1); nevertheless, the engine control is deviated toward the rich side.

The reasons for the above-mentioned (1) are as follows:

The exhaust gas from the CNG engine has a larger content of hydrogen than the gasoline engine in all regions. Therefore, when the capability of oxidizing hydrogen is decreased in the second protective layer, hydrogen passes through the first and second protective layers to reach the detection electrode. In this case, a hydrogen molecule is lighter than an oxygen molecule. Since the diffusion rate of the hydrogen molecule is larger than that of the oxygen molecule, the concentration of hydrogen is relatively higher than the concentration of oxygen around the detection electrode. Accordingly, the oxygen around the detection electrode is consumed to decrease the oxygen partial pressure. It is supposed that the control point of the oxygen sensor is deviated toward the lean side because of a diffusion difference of hydrogen and oxygen in the protective layers.

The reasons for the above-mentioned (2) are as follows:

By continuously using the oxygen sensor, the detection electrode metal is sintered or sublimated, the effective area of the electrode is reduced, and oxidation, i.e., burning reaction of a large amount of methane contained in the exhaust gas is insufficient. Although the exhaust gas is actually in a rich state, due to incomplete combustion, oxygen remains around the detection electrode, and the oxygen partial pressure is not lowered. As a result, the control point of the oxygen sensor is supposedly deviated to the rich side.

Moreover, as described in (2), although the protective layer is formed, the detection electrode metal is sintered or sublimated for the following reasons:

The sintering of the detection electrode metal progresses regardless of the presence of the protective layer mainly because it depends on oxygen concentration and temperature. On the other hand, sublimation depends on reducible gas, temperature and gas flow rate. Therefore, sublimation is related with the presence of the protective layer to some degree, but remarkably progresses if the catalyst capability of the protective layer is deteriorated. As aforementioned, the exhaust gas of CNG engine contains a large amount of hydrogen, but hydrogen has a strong reducing force. Therefore, if the capability of oxidizing hydrogen of the second protective layer is lowered at a high temperature and a high flow rate, the amount of hydrogen reaching the detection electrode is increased, and the detection electrode metal tends to easily sublime.

SUMMARY OF THE INVENTION

Wherefore, an object of the present invention is to provide a preferable oxygen sensor disposed before an exhaust gas purifying catalyst of an engine which uses a hydrocarbon containing fuel with a ratio of hydrogen atoms and carbon atoms, i.e., H/C ratio of three or more.

To attain this and other objects, the present invention provides an oxygen sensor disposed before an exhaust gas purifying catalyst of an engine which uses a fuel containing a hydrocarbon having a ratio of hydrogen atoms and carbon atoms, i.e., H/C ratio of three or more. The oxygen sensor is provided with a reference electrode disposed on a surface of a solid electrolytic body having an oxygen ion conductivity, a detection electrode with a thickness of 1 to 2 $\mu$m disposed on the other surface of the solid electrolytic body and formed only of a metal which promotes oxidizing reaction of the hydrocarbon, a first porous protective layer for covering the detection electrode, and a second porous protective layer disposed in or on the first protective layer to carry 0.5 to 7 mol % of a catalyst which promotes oxidizing reaction of hydrogen.

The exhaust gas of the engine using the fuel containing the hydrocarbon such as methane or ethane with the H/C ratio of three or more contains a larger amount of hydrogen $H_2$ in all exhaust gas flow regions as compared with the exhaust gas of a gasoline engine. In the oxygen sensor of the present invention, even if the exhaust gas contains a large amount of hydrogen, the second protective layer carries a large amount of catalyst in the range of 0.5 to 7 mol %. Therefore, even after long-time use, the catalyst is not easily sublimated or scattered, and the capability of oxidizing hydrogen $H_2$ is not easily lowered. Therefore, the hydrogen in the exhaust gas is oxidized or burnt in the second protective layer, and there is only little amount of hydrogen which passes through the first and second protective layers to reach the detection electrode. Consequently, engine control can effectively be prevented from being largely deviated to the lean side by the influence of hydrogen in the exhaust gas.

On the other hand, on the conditions that a small load is applied and the number of revolutions is large or that a large amount of methane or another hydrocarbon is exhausted, the oxidation, i.e., burning reaction of the hydrocarbon sufficiently occurs on the detection electrode, because the detection electrode of the oxygen sensor according to the present invention is formed only of the metal which promotes the oxidizing reaction of the hydrocarbon, e.g., at least one metal selected from the group consisting of platinum, rhodium and palladium. Therefore, the oxygen around the detection electrode is consumed in accordance with the hydrocarbon concentration to lower the oxygen partial pressure. Moreover, since the thickness of the detection electrode is in the range of 1 to 2 $\mu$m, the effective area of the electrode is still maintained sufficiently even if the detection electrode metal is sintered or sublimated after the long-time use. Furthermore, since the highly reducible hydrogen contained in the exhaust gas is oxidized by a sufficient amount of catalyst carried in the second protective layer before the hydrogen reaches the detection electrode, the hydrogen scarcely reaches the detection electrode. Therefore, the detection electrode metal is hardly sublimated. Consequently, engine control can advantageously be prevented from being largely deviated to the rich side by the influence of methane or another hydrocarbon in the exhaust gas.

In the present invention, the solid electrolytic body may have bag-shaped, cup-shaped and other various configurations as long as its tip end is closed while its rear end is opened. For a solid electrolytic material, for example, $Z_rO_2$ is used. $Y_2O_3$, CaO or another stabilizing agent may be applied to $ZrO_2$.

The detection electrode and the reference electrode are both porous. The detection electrode is formed only of a metal which promotes the oxidizing reaction of hydrocarbon, e.g., at least one metal selected from the group consisting of platinum, rhodium and palladium, and its thickness is in the range of 1 to 2 $\mu$m. If the thickness is less than 1 $\mu$m, in the initial stage or after long-time operation, a large deviation toward the rich side occurs on the operating condition that a large amount of methane or another hydrocarbon is exhausted. On the other hand, if the thickness exceeds 2 $\mu$m, a large deviation toward the lean side is disadvantageously caused by the influence of a large amount of hydrogen contained in the exhaust gas. The reference electrode may be formed of the same material as that of the detection electrode, or formed mainly of the aforementioned metal.

The other surface or detection-electrode forming surface of the solid electrolytic body is preferably formed into a spherical protruded portion of a solid electrolyte. With the spherical protruded portion protruding, in the shape of wedges, into the detection electrode and the first protective layer, the first and second protective layers are firmly physically connected to the solid electrolytic body. By the provision of the spherical protruded portion, the protective layers are prevented from being easily peeled off from the solid electrolytic body, and element durability is enhanced, even if unburnt components are adsorbed by or reacted with the catalyst in the second protective layer to expand in volume. The spherical protruded portion is composed of an aggregate of granulated particles, and may be composed by forming a single layer or a composite layer of granulated particles on the surface of the base portion of the solid electrolytic body. In this case, the particle size is in the range of 40 to 100 $\mu$m, preferably in the range of 50 to 80 $\mu$m. Since a series of the spherical protruded portions forms a large amount of wedge-shaped profile, it can firmly be connected to the protective layer. If the particle size is less than 40 $\mu$m, the function of the wedge is insufficiently fulfilled. If the particle size exceeds 100 $\mu$m, the fixing force to the base portion is weakened. The spherical protruded portion may be formed by distributing the particles in such a manner that concave portions are formed among the particles. This enhances the binding force with the protective layer, and contributes to enlargement of the electrode surface area. The spherical protruded portion is preferably formed of the same material as that of the base portion of the solid electrolytic body, but may be formed of any solid electrolyte. For example, the base portion is of $ZrO_2$—$Y_2O_3$ system, and the spherical protruded portion is of $ZrO_2$—(CaO, MgO) system. Alternatively, the base portion is of $ZrzO_2$—$Y_2O_3$ system, and the spherical protruded portion is $ZrO_2$—$Y_2O_3$ system which differs from the base portion in content of $Y_2O_3$.

The first protective layer prevents the detection electrode from being expanded in volume and peeled off from the solid electrolytic body when exhaust-gas unburnt components like CO are adsorbed by or reacted with the detection electrode during operation. The first protective layer may be formed of ceramic such as $Al_2O_3$, spinel, BeO, $ZrO_2$, and the like or a mixture thereof, and is especially preferably formed mainly of spinel. Its porosity is about 5 to 20%, while the thickness is in the range of 100 to 180 $\mu$m, preferably about 150 $\mu$m. Additionally, the thickness of the first protective layer in the element tip end may be larger, for example, ⅗ to twice larger than the thickness thereof in the element rear end. In this case, during low-temperature operation, irregular sensor output is avoided. Specifically, by suppressing the generation of so-called chemical noises, control is performed more accurately even during the low-temperature operation. The axial length of the first protective layer may be selected from the range of ⅕ to ½ of the axial length between the element tip end and the element attachment portion. A different material may be used for a portion of thick section.

The first protective layer does not necessarily have to carry the catalyst which promotes the oxidation of unburnt components of exhaust gas. If the catalyst is carried by the first protective layer, however, the catalyst in the first protective layer can preferably function even after the catalyst in the second protective layer is scattered or sublimated.

In the case where the catalyst is carried in the first protective layer, the catalyst is preferably composed mainly of platinum (Pt), for example, 80 wt % or more of Pt. Additionally, the amount of carried catalyst may be in the range of 0.01 to 5 wt % relative to the total amount of the materials constituting the first protective layer. If the amount is less than 0.01 wt %, no effect is expected. If the amount exceeds 5 wt %, air permeability of the first protective layer may be lost. However, in a case of exposure to dense or rich exhaust gas, the amount is preferably 1 wt % or less. If the amount exceeds 1 wt %, a large amount of unburnt components are adsorbed by or reacted with the noble-metal catalyst to generate a crack in the protective layer. The catalyst can be dispersed uniformly or non-uniformly over the protective layer. For example, the content of noble metals may be increased in the element tip end which contains a large amount of unburnt components of the exhaust gas. Additionally, the material of the catalyst may differ with each portion.

The second protective layer is formed, for example, by a refractory material like a metal oxide. As the metal oxide, besides alumina, magnesia or another general metal oxide, a non-stoichiometric transition metal oxide may be used. In a case where the non-stoichiometric transition metal oxide is used, if the catalyst is carried in the first protective layer, the catalyst is prevented from being scattered during operation so as to prevent λ point deviation or output decrease. Moreover, the catalyst action peculiar to the transition metal of the second protective layer itself and the action of the carried catalyst of the second protective layer further promotes the oxidizing action of the unburnt components of the exhaust gas. Additionally, the non-stoichiometric characteristics of the transition metal change the distribution of electrons or positive holes in accordance with the oxygen amount. Therefore, the unburnt components are prevented from being excessively adsorbed by the catalyst, and the action of the carried catalyst can be kept stable for a long time. Any oxide of transition metal in groups 3A–7A and 8 can selectively be used as long as the aforementioned action is fulfilled, but an oxide of a metal of group 4A or 8, e.g., titanium (Ti), cobalt (Co) or nickel (Ni) is preferable. Especially, a non-stoichiometric titania represented by TiOx may be used, in which x is in the range of 1.8 to 2, preferably 1.95 to 2, 2 being excluded in either case, because it can fulfill the above-mentioned action, and is superior in thermal resistance. The content of titania (TiOx) is 50 wt % or more, preferably 70wt % or more relative to the total amount of the materials constituting the is second protective layer excluding the carried catalyst. In this case, the remaining part is formed of another non-stoichiometric transition metal oxide, but may be formed of a stoichiometric transition metal oxide or a ceramic material similar to the material of the first protective layer. The porosity of the second protective layer may be set larger than that of the first protective layer so that the gas to be measured can easily reach the detection electrode and sensor responsivity are prevented from being deteriorated. For example, the porosity may be in the range of 8% to 15%, and through holes may be formed in the second protective layer. In this respect, the second protective layer may be thinner than the first protective layer. For example, the thickness of the second protective layer is in the range of 10 to 50 µm.

The amount of catalyst carried in the second protective layer needs to be in the range of 0.5 to 7 mol % relative to the entire second protective layer. If the amount is less than 0.5 mol %, in the initial stage or after long-time operation, a large amount of hydrogen contained in the exhaust gas is not sufficiently burnt in the second protective layer. The engine control disadvantageously causes a large deviation toward the lean side by the influence of the unburnt hydrogen. On the other hand, if the amount exceeds 7 mol %, a crack may be generated in the second protective layer. The catalyst is not especially limited as long as it promotes the oxidizing reaction of hydrogen, but at least one selected from the group consisting of platinum, rhodium and palladium is preferable.

According to the present invention, the output voltage of the oxygen sensor preferably exceeds a reference level for determining a rich or lean state in the atmosphere containing 3000 ppm of hydrocarbon or methane, 3000 ppm of oxygen and the remaining part of incombustible gas and on the condition that sensor temperature is 450° C. Here, the atmosphere is a model exhaust gas from an engine which uses a fuel containing a hydrocarbon with a ratio of hydrogen atoms and carbon atoms, i.e., H/C ratio of three or more. If the output voltage exceeding the reference level can be obtained using the model gas at 450° C., even in the engine control using the oxygen sensor, an excess deviation toward the rich side does not occur. If the oxygen sensor is actually mounted on the car, there will be no problem. In this case, the reference level is preferably set in the range of 400 to 600 mV. Outside the range, the engine cannot be controlled with a sufficient precision. Additionally, since the oxygen sensor of the present invention is provided with the reference electrode, the detection electrode and the first and second protective layers as aforementioned, the action described above is usually fulfilled.

DETAILED DESCRIPTION OF PREFERRED EMBODIMENT

A preferred embodiment of the present invention will now be described.

Figure 1:
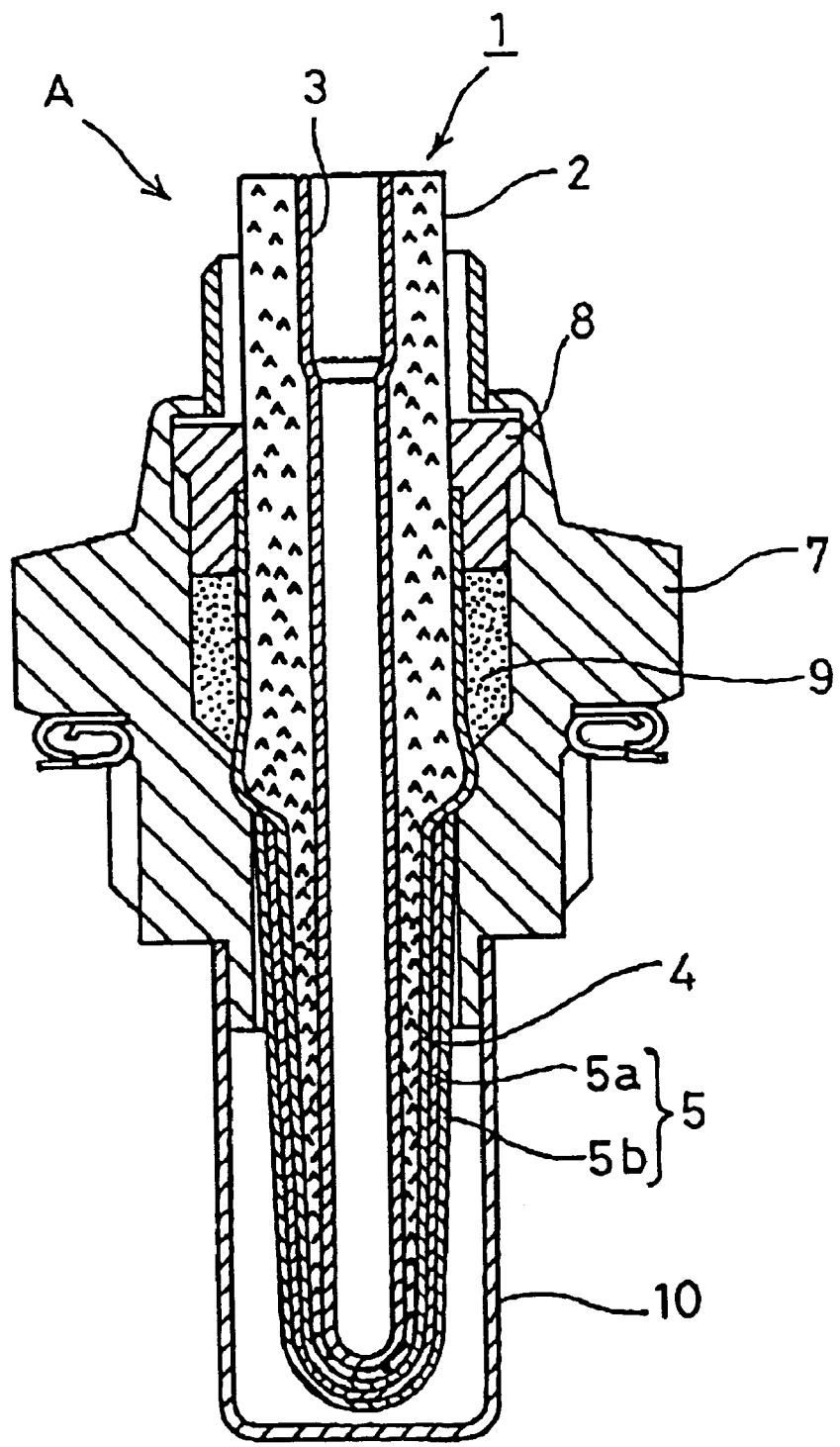
FIG. 1 is a sectional view of an oxygen sensor according to an embodiment of the present invention.
Figure 2:
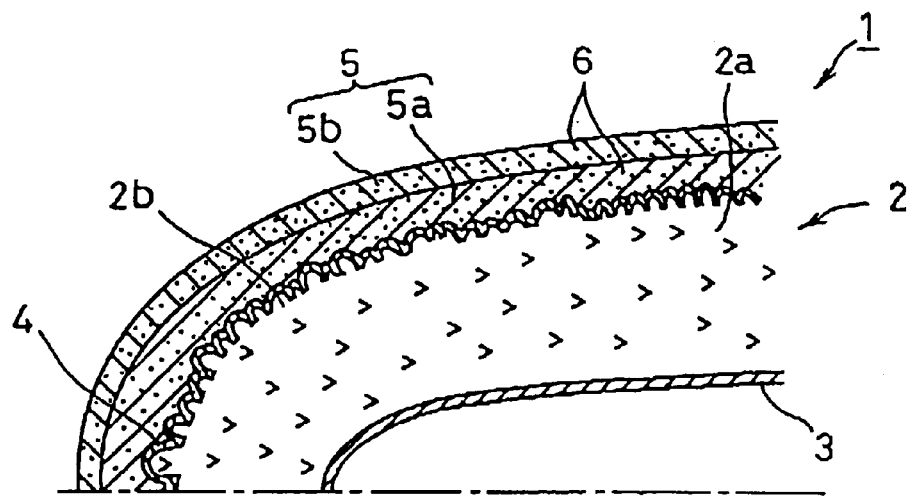
FIG. 2 is an enlarged view of a part of FIG. 1.

As shown in FIGS. 1 and 2, an oxygen sensor 1 is provided with a solid electrolytic body 2 in which a difference may be generated in oxygen concentration with reference gas and measured exhaust gas, a reference electrode 3, a detection electrode 4 and a porous protective layer 5 for covering the detection electrode 4. The reference electrode 3 and the detection electrode 4 are a pair of porous electrodes which are formed on inner and outer surfaces of the solid electrolytic body 2, respectively. The solid electrolytic body 2 is formed of $ZrO_2$ with $Y_2O_3$ applied thereto, and the reference electrode 3 and the detection electrode 4 are both Pt electrodes.

The solid electrolytic body 2 with a thickness of 1 mm is provided with a base portion 2a and a spherical protruded portion 2b positioned on the outer surface of the base portion 2a. The detection electrode 4 with a thickness of 1.2 µm and further the protective layer 5 are formed in accordance with the configuration of the spherical protruded portion 2b. The protective layer 5 is provided with a 200 µm thick first protective layer 5a positioned inward to directly cover the detection electrode 4 and a 100 µm thick second protective layer 5b positioned outward to be exposed to the exhaust gas. In the protective layer 5, only the second protective layer 5b carries a Pt catalyst 6 which promotes the oxidizing reaction of hydrogen. The amount of carried catalyst is 2 mol % relative to the whole of the second protective layer 5b. Additionally, the first protective layer 5a is a flame-sprayed layer of spinel, while the second protective layer 5b is a metal oxide layer of titania.

Additionally, as shown in FIG. 1, the oxygen sensor 1 is held in a housing 7 via a filler 9 and a caulking ring 8. The tip end of the housing 7 is provided with a protective tube 10 for protecting the oxygen sensor 1.

The output voltage of the oxygen sensor 1 exceeds a reference level of, for example, 500 mV for determining a rich or lean state in the atmosphere containing 3000 ppm of methane, 3000 ppm of oxygen and the remaining part of nitrogen gas and on the condition that sensor temperature is 450° C. Therefore, even if engine control is performed using the oxygen sensor 1, an excess deviation toward the rich side may not occur. If the oxygen sensor 1 is actually mounted on the car, there will be no problem.

A method of manufacturing an oxygen sensor element according to the present invention will next be described. After 5 mol % of $Y_2O_3$ with a purity of 99.9% is applied to and mixed with $ZrO_2$ with a purity of 99% or more, calcination is performed for two hours at 1300° C. Subsequently, the calcined material is wet-powdered in a ball mill with water applied thereto until 80% of particles have a particle diameter of 2.5 µm or less. Subsequently, a water-soluble binder is applied to the powdered material, and spherical particles with an average particle diameter of 70µm are obtained through spray drying. The particles are rubber-pressed to form a desired tubular configuration. After drying, grinding is performed using a grinding stone to shape the predetermined configuration. Subsequently, the slurry which is obtained by applying a water-soluble binder fibrin sodium glycolate and a solvent to the particles is attached onto the outer surface of the tubular shaped material to obtain a formed material. After the formed material is dried, it is sintered for two hours at 1500° C. to obtain a zirconia ceramic material. A detecting portion has an axial length of 20 mm, an outer diameter of about 5 mm and an inner diameter of about 4 mm.

Through chemical plating, Pt layers each having a thickness of 1.2 µm are deposited on inner and outer surfaces of the zirconia ceramic material, and subsequently baked at 1000° C. Additionally, the inner Pt layer forms the reference electrode, while the outer Pt layer forms the detection electrode.

Subsequently, the first protective layer with a thickness of about 200 µm is formed on the detection electrode by plasma spray coating of spinel powder MgO•$Al_2O_3$. Thereafter, a noble-metal containing titania paste is applied onto the surface of the first protective layer. By baking at 800° C. in the reducing atmosphere, the second protective layer with a thickness of about 100 µm having about 2 µm pores is formed.

The paste is obtained by immersing titania powder in $H_2PtCl_6$ solution or Pt black, and then, drying and impregnating are performed while stirring, and subsequently an organic binder and a solvent of butyl carbitol are applied.

After the oxygen sensor 1 obtained as aforementioned is inserted into the housing 7, the caulking ring 8 and the filler 9 such as talc are inserted to fix the oxygen sensor 1 in the housing 7. Subsequently, the tip end of the oxygen sensor 1 is covered with the protective tube 10, and the tip end of the housing 7 and the rear end of the protective tube 10 are welded. Then, terminals and lead wires (not shown) are connected to the electrodes, and an outer cylinder (not shown) is mounted on the oxygen sensor element.

EXAMPLES OF EXPERIMENT

The following experiments were carried out based on the oxygen sensor element according to the embodiment of the present invention to inspect each evaluation item. Moreover, comparative examples were similarly inspected.

FIRST EXPERIMENT

Figure 3:
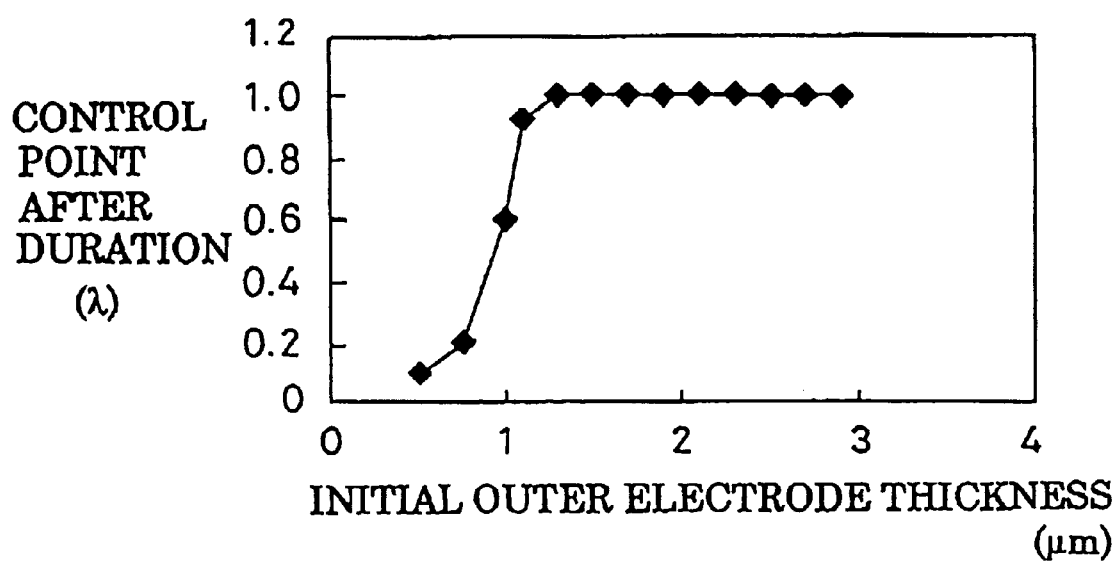
FIG. 3 is a graph showing the relationship of a detection electrode thickness and a control point in the atmosphere of $CH_4$—$O_2$.

The oxygen sensor elements with the thickness of the detection electrode variously changed were prepared, the control point $\lambda$ in the atmosphere of $CH_4$—$O_2$ was checked, and the relationship of an initial detection electrode thickness and the control point after duration was evaluated. Results are shown in the graph of FIG. 3. Additionally, the term "after duration" means that the oxygen sensor element is heated to 850° C. and retained for 1000 hours in the rich atmosphere, i.e., the atmosphere containing the excess amount of fuel.

The control point $\lambda$ in the atmosphere of $CH_4$—$O_2$ which raises no problem when the oxygen sensor element is actually mounted on the car is 0.5 or more. As seen from the graph of FIG. 3, the detection electrode may have a thickness of 1 µm or more.

SECOND EXPERIMENT

Figure 4:
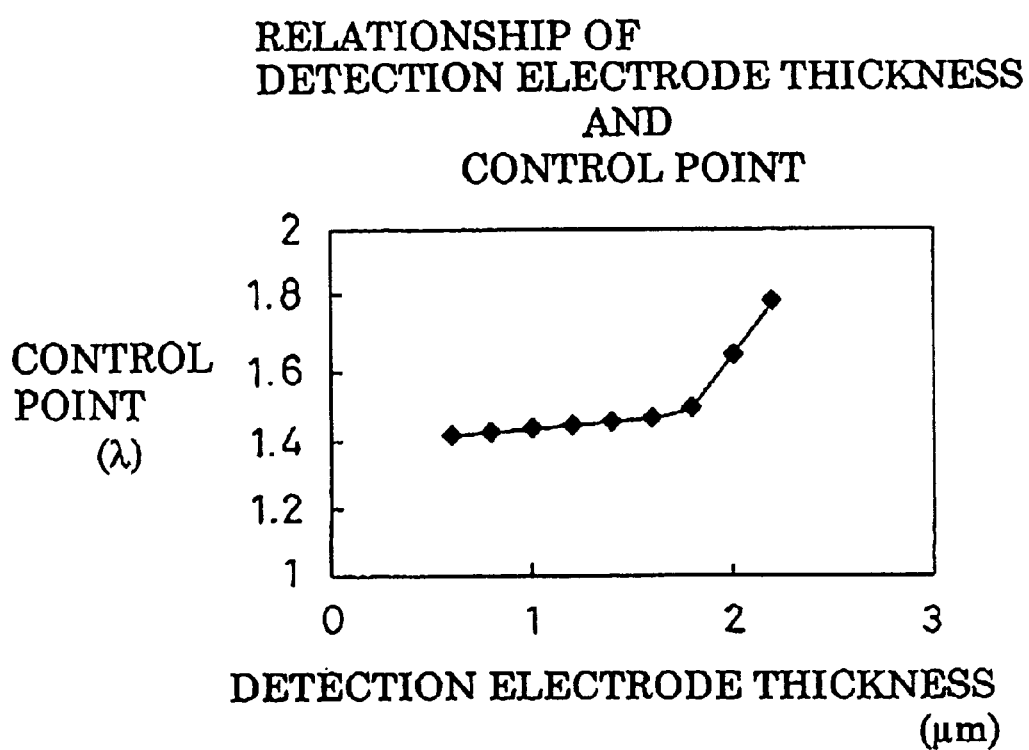
FIG. 4 is a graph showing the relationship of a detection electrode thickness and a control point in the atmosphere of $H_2$—$O_2$.

The oxygen sensor elements with the thickness of the detection electrode variously changed were prepared, the control point $\lambda$ in the atmosphere of $H_2$—$O_2$ was checked, and the relationship of the detection electrode thickness and the control point was evaluated. Results are shown in the graph of FIG. 4.

The control point $\lambda$ in the atmosphere of $H_2$—$O_2$ which raises no problem when the oxygen sensor element is actually mounted on the car is 1.6 or less. If the detection electrode thickness exceeds 2 µm, the control point is exceeded. Therefore, the detection electrode thickness needs to be 2 µm or less.

THIRD EXPERIMENT

Figure 5:
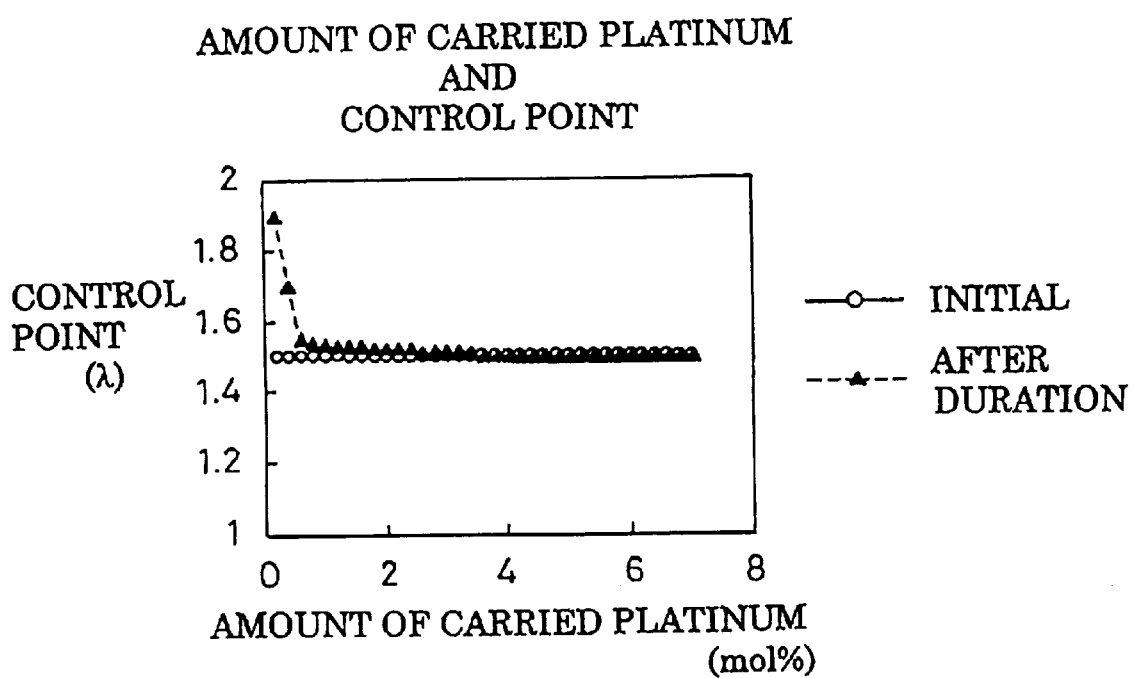
FIG. 5 is a graph showing the relationship of the amount of carried platinum and a control point in the atmosphere of $H_2$—$O_2$.

The oxygen sensor elements with the amount of the platinum carried in the second protective layer variously changed were prepared, the control point $\lambda$ in the atmosphere of $H_2$—$O_2$ was checked, and the relationship of the amount of carried platinum and the control point was evaluated. Results are shown in the graph of FIG. 5.

The control point $\lambda$ in the atmosphere of $H_2$—$O_2$ which raises no problem when the oxygen sensor element is actually mounted on the car is 1.6 or less. This shows that even if the amount of carried platinum is about 0.02 mol % in the initial stage, i.e., before duration, a sufficient effect is obtained. However, to obtain a sufficient effect even after the oxygen sensor element is heated to 850° C. and retained for 1000 hours in the rich atmosphere, the amount of carried platinum needs to be 0.5 mol % or more. Additionally, if the amount of carried platinum exceeds 7 mol %, a crack may be generated in the second protective layer. Therefore, the amount of carried platinum needs to be 7 mol % or less.

The present invention is not limited to the embodiment described above. Modifications of the invention herein disclosed will occur to a person skilled in the art and all such modifications are deemed to be within the scope of the invention as defined by the appended claims.

What is claimed is:

1. An oxygen sensor for use with an impinging gas comprising hydrocarbons comprising:
   a reference electrode disposed on a first surface of a solid electrolytic body having an oxygen ion conductivity;
   a detection electrode with a thickness of greater than 1 $\mu$m and less than 2 $\mu$m disposed on a second surface of said solid electrolytic body and formed only of a metal which promotes oxidizing reaction of said hydrocarbon;
   a first porous protective layer for covering said detection electrode; and
   a second porous protective layer disposed on said first protective layer to carry 0.5 to 7 mol % of a catalyst which promotes oxidizing reaction of hydrogen.

2. The oxygen sensor according to claim 1 wherein said metal which promotes the oxidizing reaction of the hydrocarbon is at least one selected from the group consisting of platinum, rhodium and palladium.

3. The oxygen sensor according to claim 1 wherein said catalyst which promotes the oxidizing reaction of the hydrogen is at least one selected from the group consisting of platinum, rhodium and palladium.

4. The oxygen sensor according to claim 1 wherein an output of the sensor voltage exceeds a reference level for determining a rich or lean state in the atmosphere containing 3000 ppm of methane as said hydrocarbon, 3000 ppm of oxygen and the remaining part of incombustible gas and on the condition that sensor temperature is 450° C.

5. The oxygen sensor according to claim 4 therein said reference level is set in the range of 400 to 600 mV.

6. The oxygen sensor according to claim 1 wherein the solid electrolytic body is defined by an enclosed tip end and an open rear end forming a cup-shaped configuration having an outer protruding spherical surface portion and an inner base portion.

7. The oxygen sensor according to claim 6 wherein the outer protruding spherical portion of the electrolytic body is composed of an aggregate of granulated particles disposed as a composite layer on the inner base portion of the electrolytic body, the granulated particle size having a range of 40 to 100 $\mu$m.

8. The oxygen sensor according to claim 7 wherein the outer protruding spherical portion of the electrolytic body is a different electrolytic compound than that of the base portion.

9. The oxygen sensor according to claim 1 wherein the solid electrolytic body is formed of $Z_rO_2$.

10. The oxygen sensor according to claim 9 wherein the solid electrolytic body formed of $Z_rO_2$ is stabilized by the application of one of $Y_2O_3$ and CaO.

11. The oxygen sensor according to claim 1 wherein the first protective layer has a porosity of about 5 to 20% and a thickness of between 100 to 180 $\mu$m.

12. The oxygen sensor according to claim 1 wherein the first protective layer is a ceramic material selected from the group consisting of $Al_2O_3$, spinel, BeO and $Z_rO_2$.

13. The oxygen sensor according to claim 1 wherein the first protective layer carries a catalyst, the catalyst being about 80 wt % or more of platinum and within a range of 0.01 to 5 wt % of the material constituting the first protective layer.

14. The oxygen sensor according to claim 1 wherein the second protective layer is formed of an oxide of a transition metal selected from the group consisting of groups 3A–7A and 8.

15. The oxygen sensor according to claim 14 wherein the second protective layer is formed of a nonstoichiometric titania represented by $TiO_x$, wherein x is in a range of 1.8 to 2.

16. The oxygen sensor according to claim 1 wherein the second protective layer has a porosity greater than that of the first protective layer, within a range of about 8 to 15% and a thickness of 10 to 50 $\mu$m such that the impinging gas can more easily reach the detection electrode.

17. The oxygen sensor according to claim 1 wherein the first porous protective layer does not contain any catalyst to promote oxidizing reaction of hydrogen.

18. An oxygen sensor disposed upstream of an exhaust gas purifying catalyst of an engine, the engine using a fuel containing a hydrocarbon having a ratio of hydrogen atoms and carbon atoms of three or more, the oxygen sensor comprising;
   a reference electrode disposed on a first surface of a solid electrolytic body having an oxygen ion conductivity;
   a detection electrode with a thickness of greater than 1 $\mu$m and less than 2 $\mu$m disposed on a second surface of said solid electrolytic body and formed only of a metal which promotes oxidizing reaction of said hydrocarbon;
   a first porous protective layer for covering said detection electrode; and
   a second porous protective layer disposed on said first protective layer to carry 0.5 to 7 mol % of a catalyst which promotes oxidizing reaction of hydrogen.

19. The oxygen sensor according to claim 18 wherein the fuel containing a hydrocarbon having a ratio of hydrogen atoms and carbon atoms of three or more is one of methane and ethane.

20. The oxygen sensor according to claim 18 wherein the first porous protective layer does not contain any catalyst to promote oxidizing reaction of hydrogen.

* * * * *